United States Patent
Brouwer

(10) Patent No.: US 6,715,377 B1
(45) Date of Patent: Apr. 6, 2004

(54) DRIVE SYSTEM

(75) Inventor: Stefan Frits Brouwer, Den Haag (NL)

(73) Assignee: Eaton Corporation, Cleveland, OH (US)

( * ) Notice: Subject to any disclaimer, the term of this patent is extended or adjusted under 35 U.S.C. 154(b) by 0 days.

(21) Appl. No.: 10/031,867
(22) PCT Filed: May 17, 2000
(86) PCT No.: PCT/NL00/00328
§ 371 (c)(1), (2), (4) Date: Jun. 7, 2002
(87) PCT Pub. No.: WO00/69684
PCT Pub. Date: Nov. 23, 2000

(30) Foreign Application Priority Data

May 18, 1999 (NL) .............................................. 1012087

(51) Int. Cl.⁷ ........................... F16H 55/00; A47G 1/24; G02B 7/182
(52) U.S. Cl. ........................... 74/431; 248/481; 359/872
(58) Field of Search ........................... 74/431; 248/478, 248/481, 483; 359/871, 872, 876

(56) References Cited

U.S. PATENT DOCUMENTS

| 3,609,014 A | * | 9/1971 | Kurz, Jr. ..................... 359/874 |
| 5,539,584 A | * | 7/1996 | Perry et al. .................. 359/874 |
| 5,946,151 A | * | 8/1999 | Levko ......................... 359/872 |
| 2002/0047386 A1 | * | 4/2002 | Bingle et al. .................. 310/89 |

* cited by examiner

Primary Examiner—David Fenstermacher
(74) Attorney, Agent, or Firm—Roger A. Johnston

(57) ABSTRACT

A drive system comprises a movement mechanism comprising a spherical holder (1) and a spherical bowl which, one inserted into the other, are rotatable relative to each other about an X-axis and a Y-axis, which axes lie in a plane substantially coinciding with the plane of the outside edge of the holder or extending parallel thereto. Viewed in the X-Y plane, the holder comprises two mutually perpendicular slots (4,5), provided through the holder, each of said slots having an adjusting element provided therein for motor displacement, which adjusting element is further freely movable in the bowl in a direction, viewed in the X-Y plane, perpendicular to that of the relevant slot in the holder. Through the relevant slot in the holder, the adjusting element is in an operative connection with a drive mechanism placed in the holder, which drive mechanism is connected to a motor that is likewise placed in the holder.

14 Claims, 11 Drawing Sheets

Figure 1:
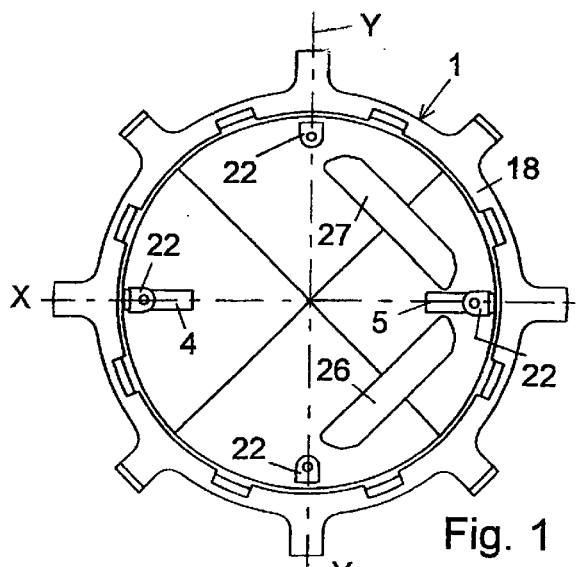
Figure 2:
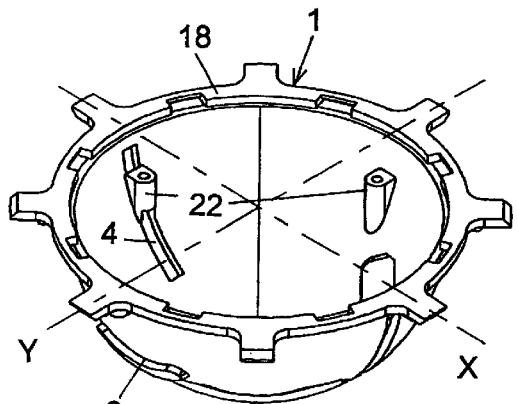
Figure 3:
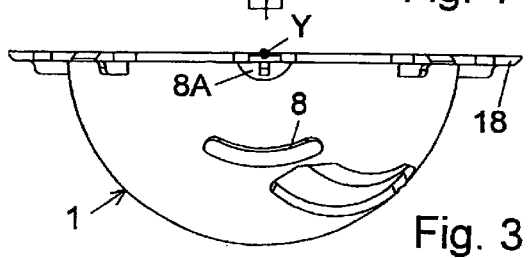
Figure 4:
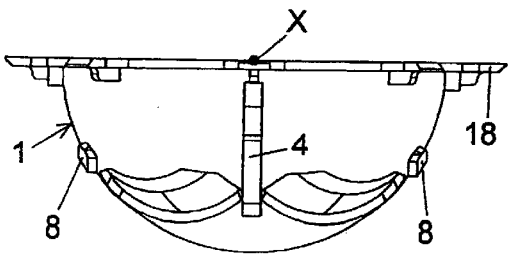
Figure 5:
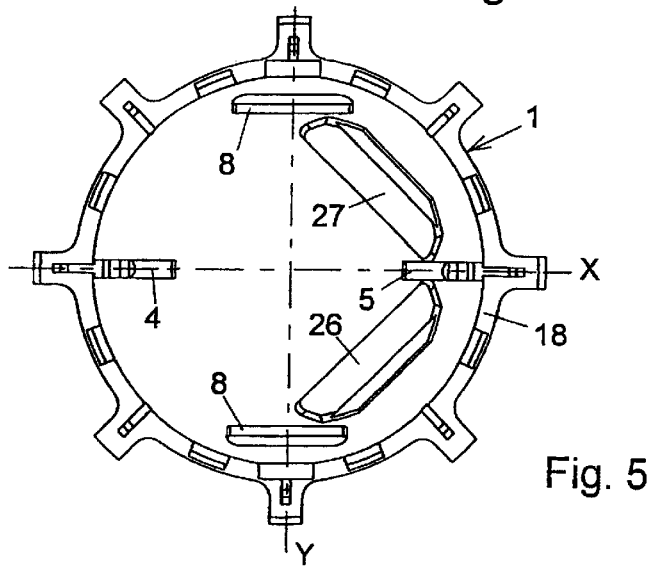
Figure 10:
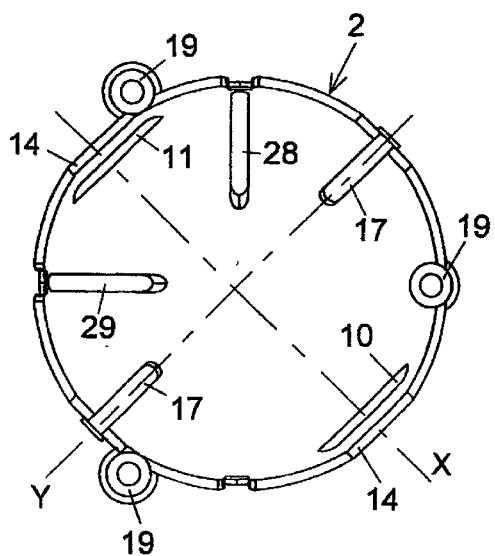
Figure 11:
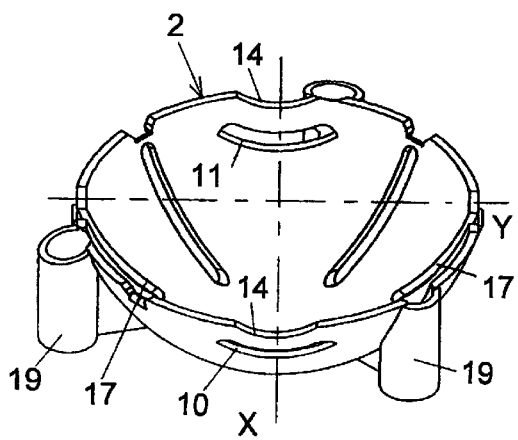
Figure 12:
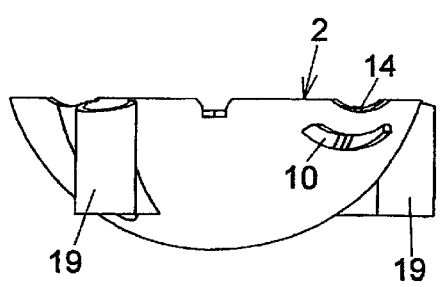
Figure 13:
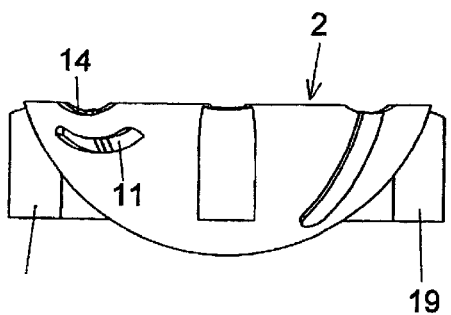
Figure 25:
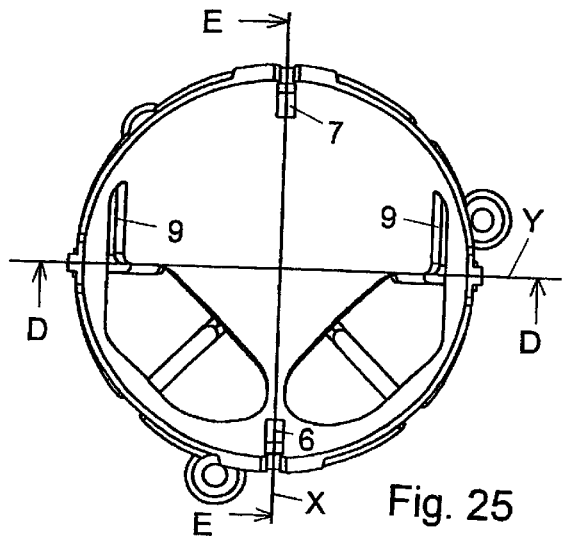
Figure 28:
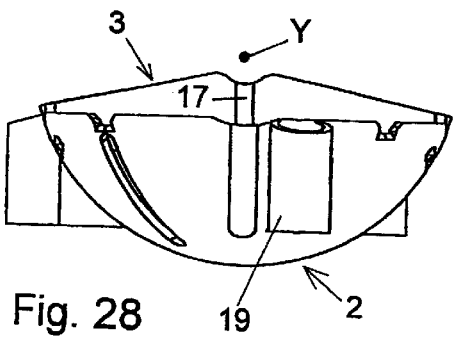

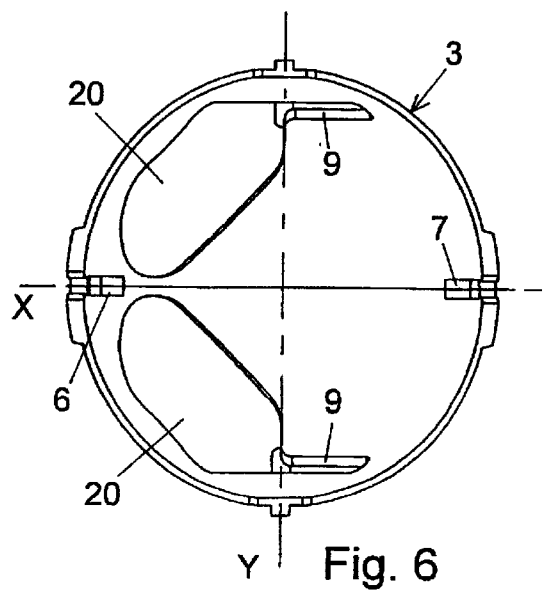
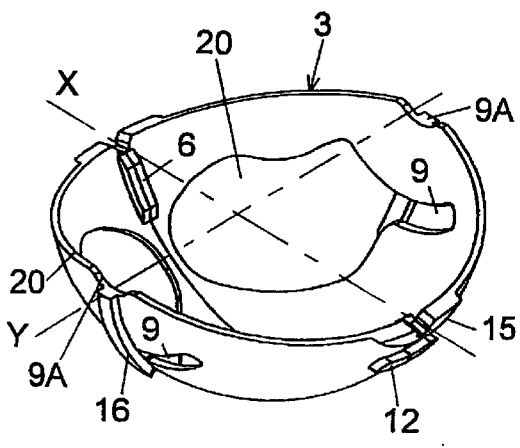
Fig. 6    Fig. 7
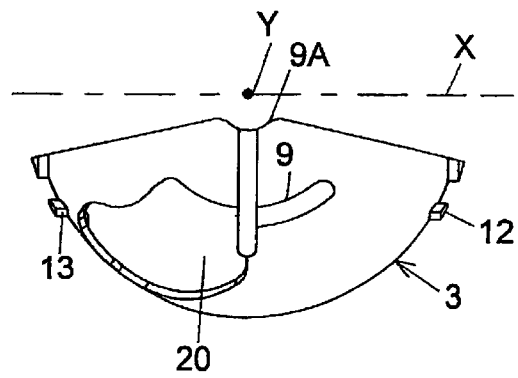
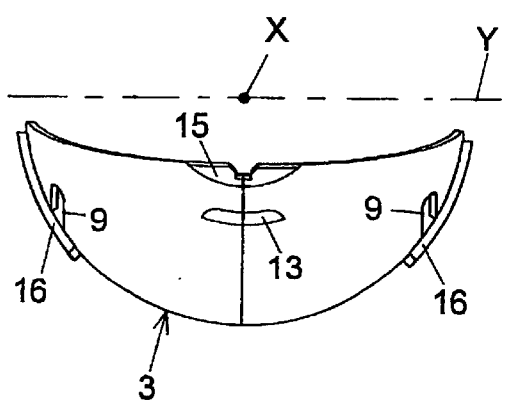
Fig. 8    Fig. 9

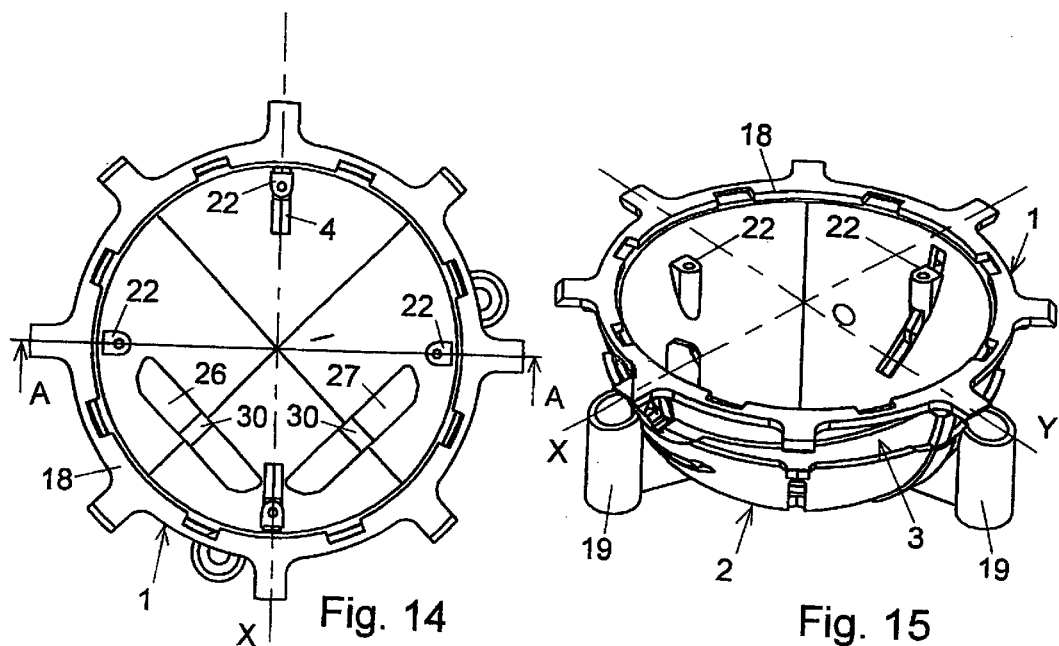
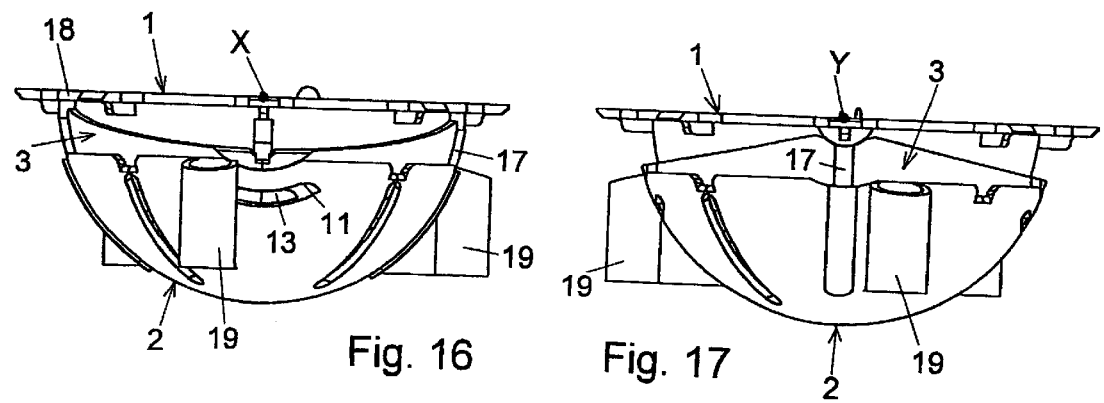
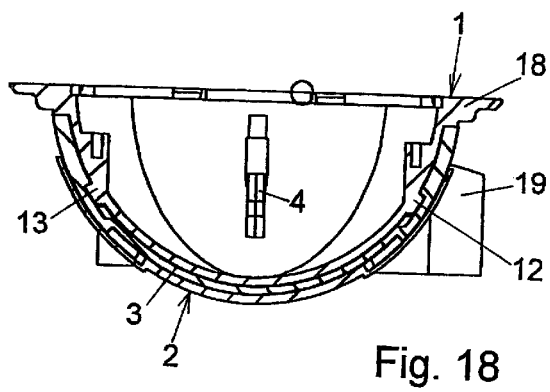

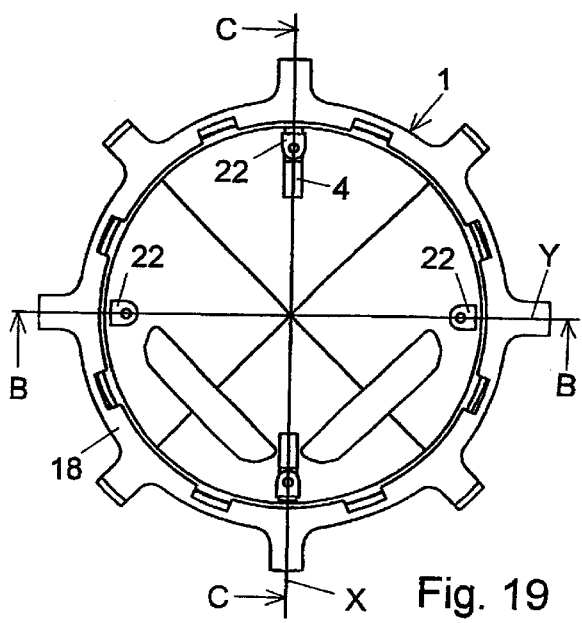
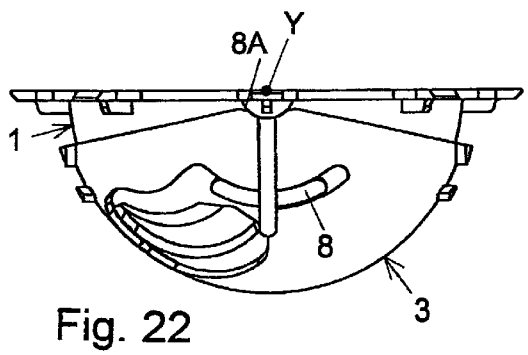
Fig. 22
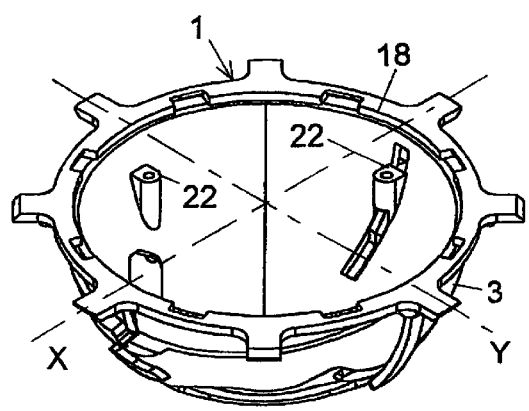
Fig. 23
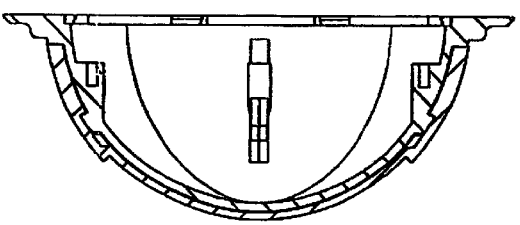
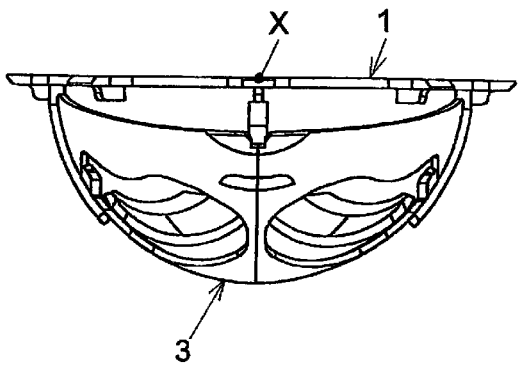
Fig. 21
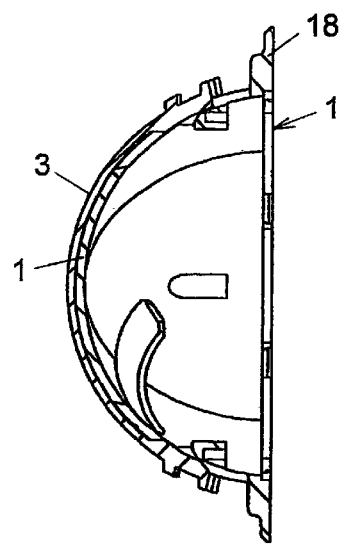
Fig. 24

DRIVE SYSTEM

The present invention relates to a drive system for a movement mechanism comprising a spherical holder and a spherical bowl, which, one inserted into the other, are rotatable relative to each other about a first axis, the X-axis, and a second axis, the Y-axis, which axes lie in a plane substantially coinciding with the plane of the outer edge of the holder or extending parallel thereto, the holder, viewed in the X-Y plane, being provided with two mutually perpendicular slots, the drive system further comprising adjusting elements and drive mechanisms placed in the holder, each of said drive mechanisms being connected to a motor that is likewise placed in the holder to drive an adjusting element such that the holder and the bowl are rotated relative to each other.

Such a drive system is known from WO-A-98 31565. The holder and the bowl are rotatable relative to each other by means of two pinions, each of which being relatively connected with a rack, provided at the inner side of the bowl, through slots in the holder. A combined movement of the holder and the bowl relative to each other about two axes is possible, but requires a mechanism that is rather costly to manufacture from injection moulded parts.

The object of the invention is to realize an accurate an reliable motor drive of the holder relative to the bowl, which drive is moreover of a highly compact design.

To that end, in accordance with the invention, the drive as described in the preamble is characterized in that the bowl, viewed in the X-Y plane, comprises two mutually perpendicular slots, each slot in the holder, viewed in the X-Y plane, being perpendicular to a corresponding slot in the bowl, each adjusting member being freely movable in the bowl and in an operative connection with a relevant drive mechanism through the relevant slot in the holder.

The slots in the bowl and the holder can be provided in such a manner that the direction of movement of the adjusting elements in the bowl extends from the adjusting elements in the bowl extends from the circumferential edge of the bowl to the center of the bowl. The corresponding slots in the holder are perpendicular hereto, viewed in the X-Y plane. It is also possible that the direction of movement of the adjusting elements in the holder extends from the circumferential edge of the holder to the center of the holder. Accordingly, the corresponding slots in the bowl are perpendicular hereto, viewed in the X-Y plane.

In particular when stepping motors are used, it is preferred that the adjusting elements be arranged so as to be displaceable at an angle of 45° relative to the X-axis and the Y-axis. When standard dc-motors are used, it suffices to arrange the adjusting elements so as to be displaceable at an angle of 9° relative to the X-axis and the Y-axis.

For the adjusting elements and the displacement thereof, various embodiments are possible. In a first embodiment, the adjusting elements are displaced by a rodshaped drive mechanism, while by the motor, via a transmission system, a rod can be moved back and forth for displacing thereby the adjusting element through the slot in the holder. In a second embodiment, the adjusting elements are designed as toothed elements. Each of the thoothed elements can be formed by a ring segment having, for instance, internal teeth, crown teeth, or bevel gear teeth.

A particulary compact construction of the movement mechanism is obtained when it further comprises a dish located between the holder and the bowl, which dish is connected to the bowl for rotation about the X-axis only and which is connected to the holder for rotation about the Y-axis only. For the use in a wing mirror for a vehicle, an adjusting plate for a mirror can be fixed on the holder. Since the motor and the drive mechanism are fitted in the holder as well, the holder with the components arranged therein and secured thereon can be snapped in the bowl as a unit. The latter construction further enables providing the holder with an electric plug terminal, while on the adjusting plate, a separate electric terminal is present for an electric connection to the plug terminal on the holder, enabling ready through-connecting by looping.

Apart from a drive system, the invention also relates to a wing mirror for a vehicle, comprising a drive mechanism as indicated hereinabove.

Figure 29:
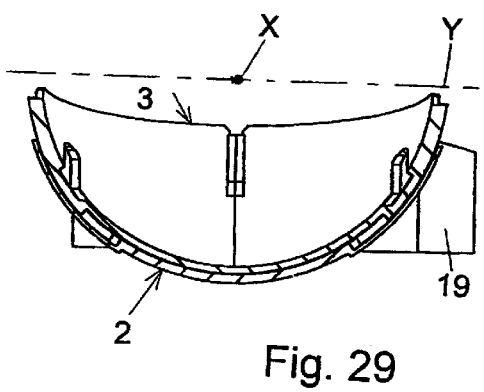
Figure 26:
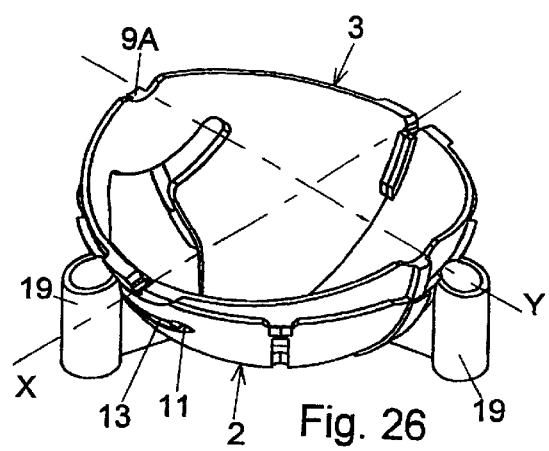
Figure 27:
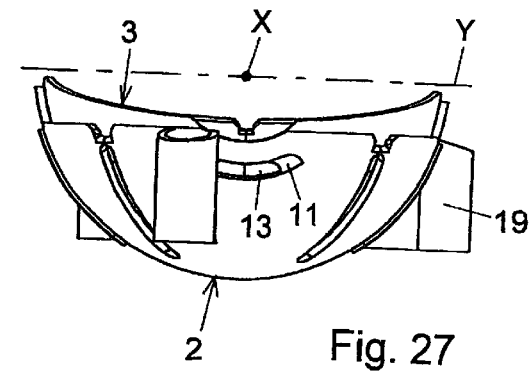
Figure 30:
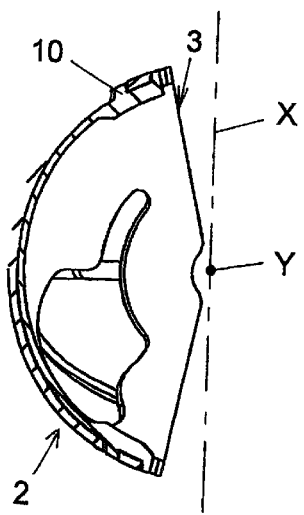
Figure 31:
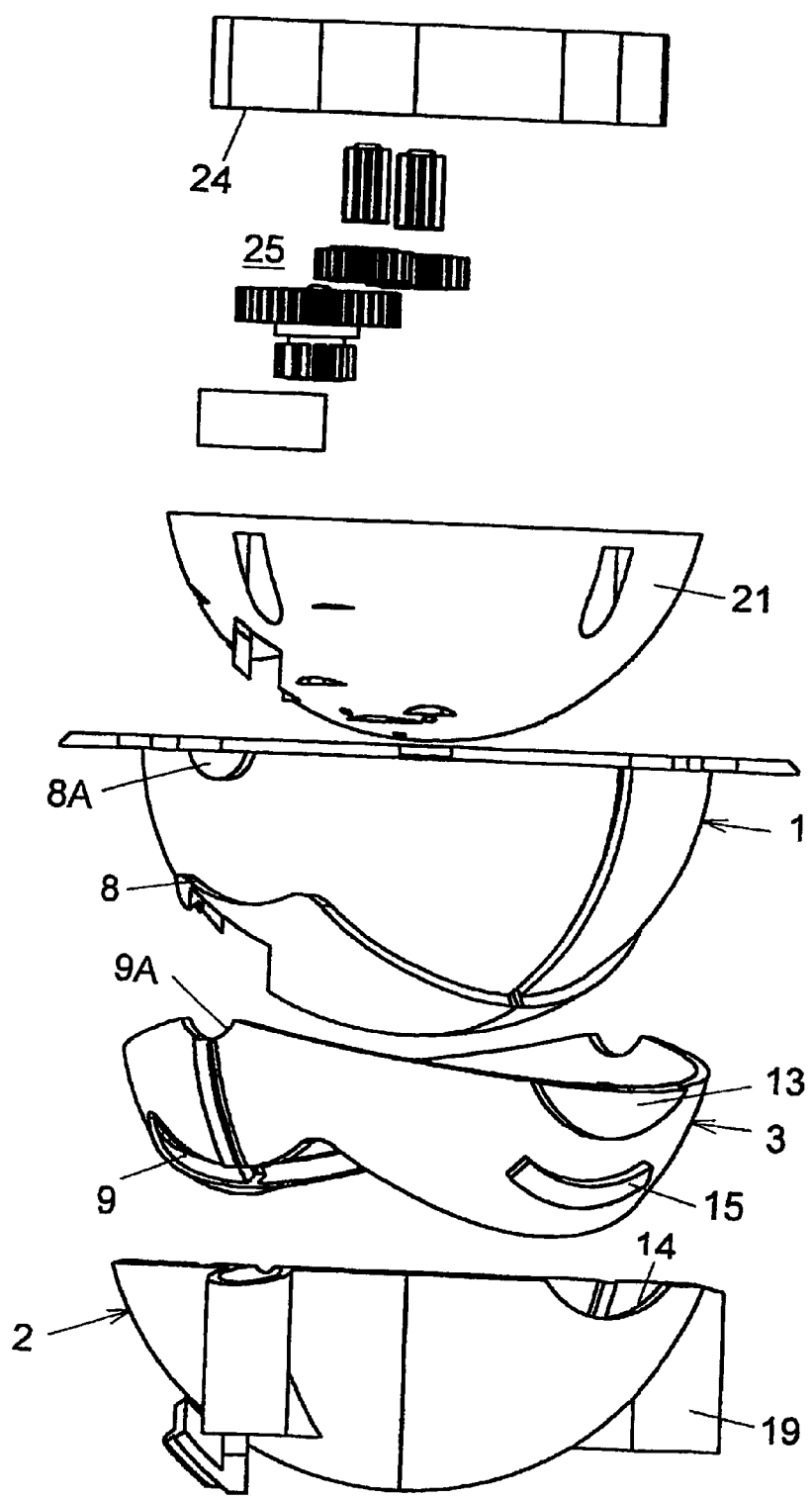
Figure 32:
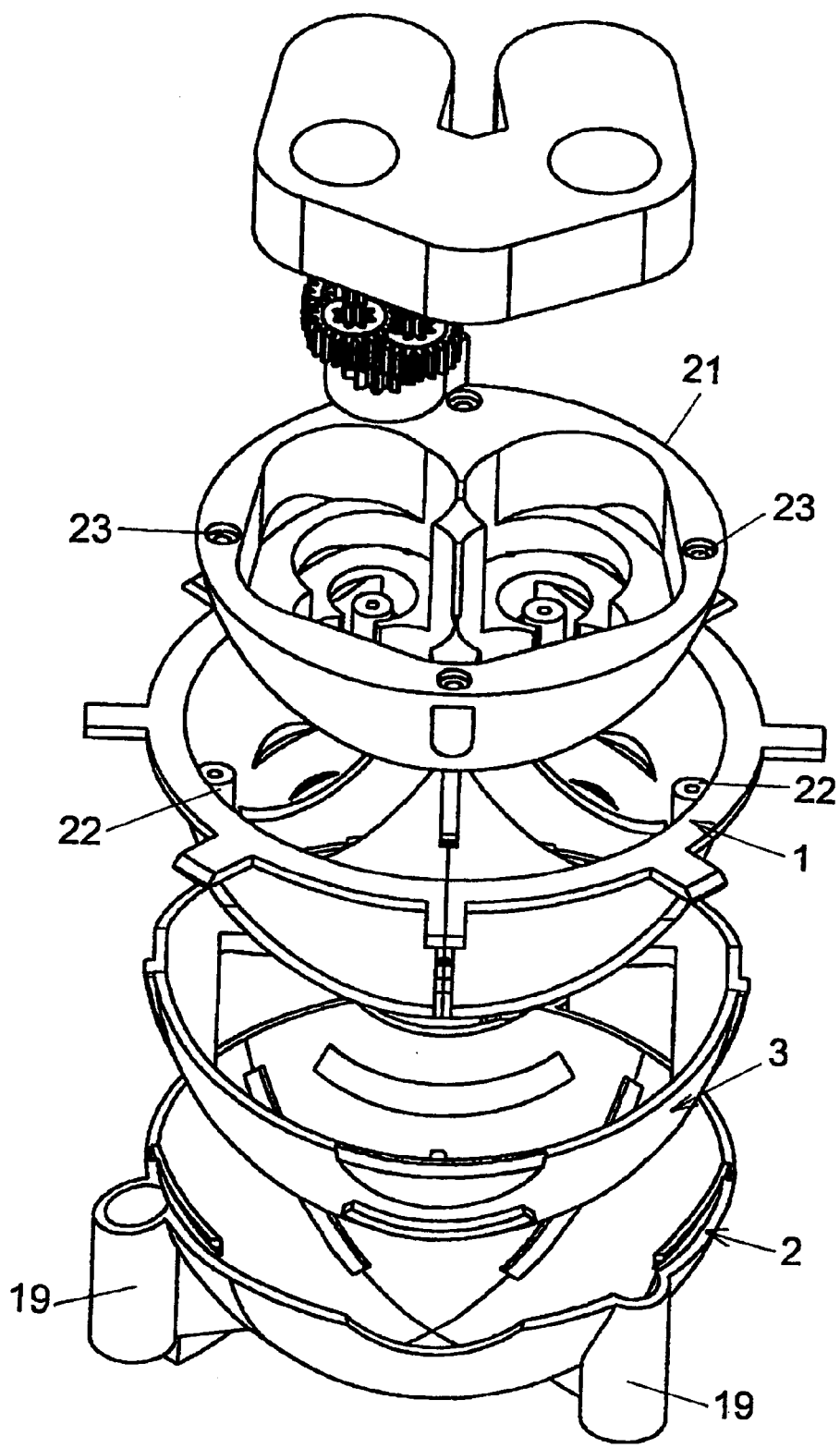
Figure 33:
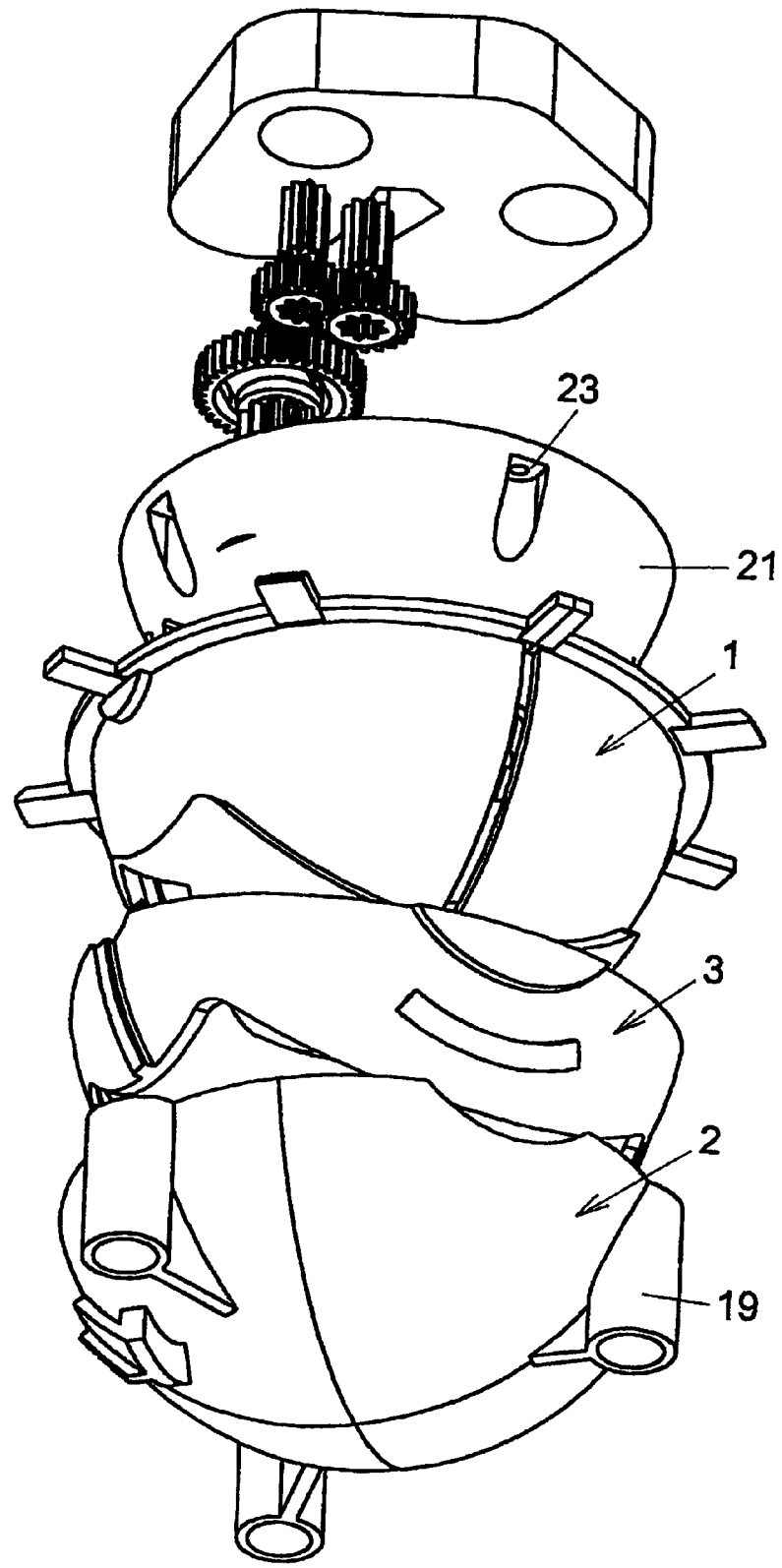
Figure 34:
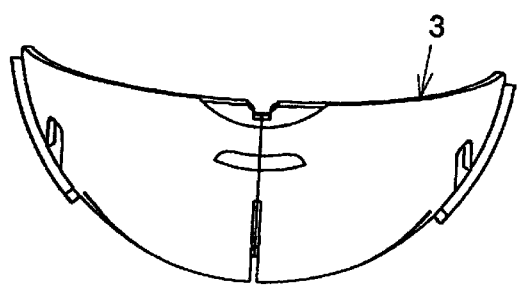
Figure 35:
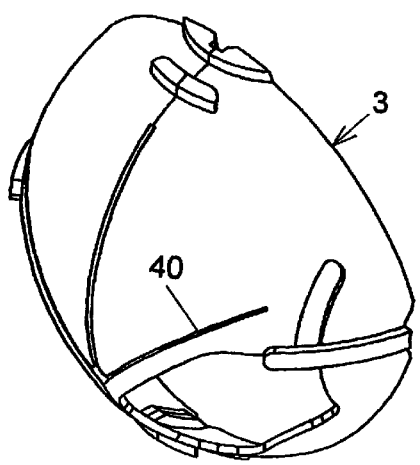
Figure 36:
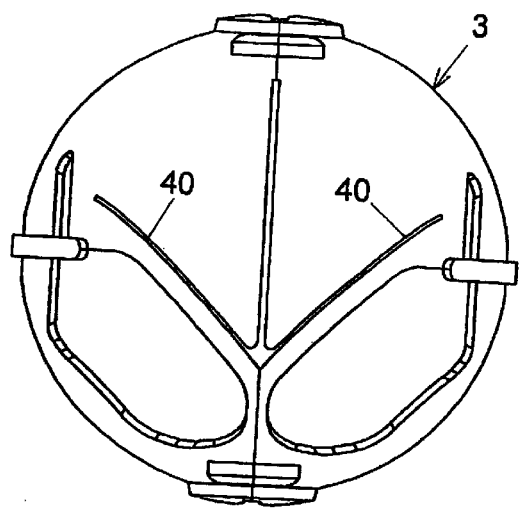
Figure 37:
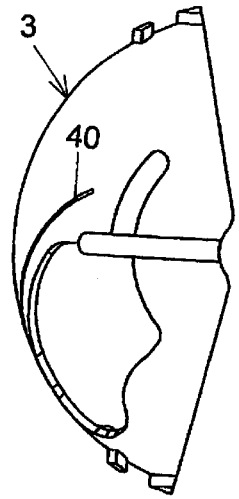
Figure 38:
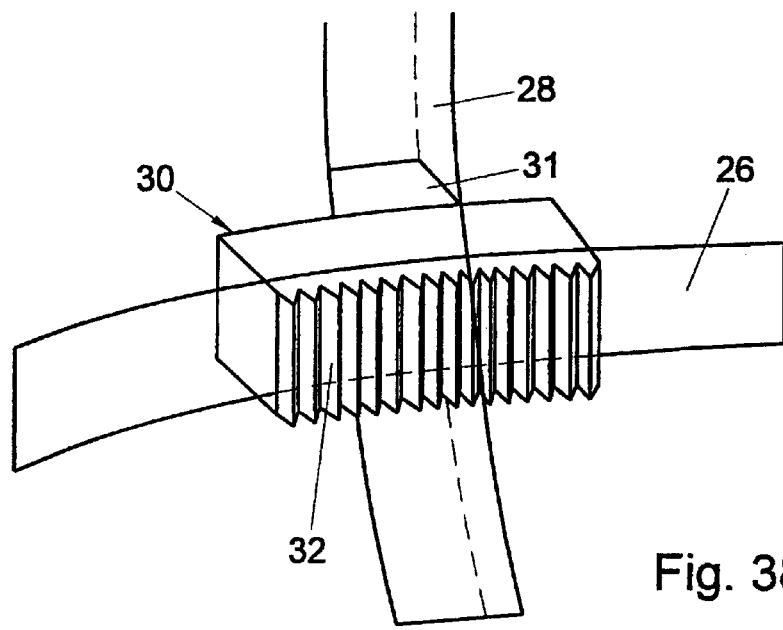
Figure 39:
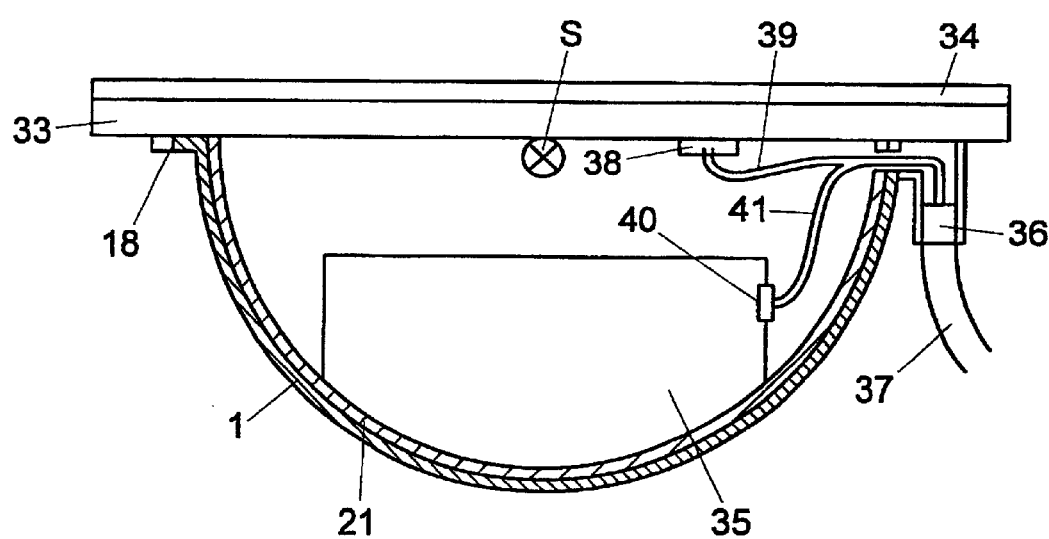

The invention will presently be specified with reference to the accompanying drawings. In these drawings:

FIGS. 1–5 represent five views of the holder;
FIGS. 6–9 represent four views of the dish;
FIGS. 10–13 represent four views of the bowl;
FIGS. 14–17 represent four views of the assembly of the holder, the dish and the bowl of FIGS. 1–13;
FIG. 18 shows a section of this assembly taken on the line A—A in FIG. 14;
FIGS. 19–22 represent four views of the assembly of the holder and the dish;
FIGS. 23 and 24 show sections taken on the line B—B and C—C respectively in FIG. 19;
FIGS. 25–28 represent four views of the assembly of the dish and the bowl;
FIGS. 29 and 30 show sections taken on the line D—D and E—E respectively in FIG. 25;
FIGS. 31–33 represent various exploded views of an actuator housing construction for a wing mirror of a vehicle;
FIGS. 34–37 represent various views of an alternative embodiment of the dish;
FIG. 38 shows the adjusting element for enabling rotating the holder and the bowl relative to each other; and
FIG. 39 schematically shows a mirror actuator according to the invention.

In the Figures, identical parts are designated by the same reference numerals.

An exemplary embodiment of the movement mechanism according to the invention, as shown in parts and in interconnection of these parts in FIGS. 1–33, comprises a spherical holder 1, a spherical bowl 2 and a dish 3. The holder, the bowl and the dish are manufactured from plastic. With the interposition of the dish 3, the holder 1 can be inserted into the bowl 2. The dish 3 is then only rotatable about the X-axis relative to the bowl 2 and only rotatable about the Y-axis relative to the holder 1, the X-axis and the Y-axis lying in a plane substantially coinciding with the outside edge of the holder 1.

To realize the rotatability of the holder 1 relative to the dish 3 about the Y-axis, two diametrically opposite slots 4 and 5 are provided in the holder 1, and the dish 3 has its inside surface provided with thickenings 6 and 7 fitting in these slots 4 and 5 respectively. Upon rotation of the holder 1 relative to the dish 3 about the Y-axis, the thickenings 6 and 7 move in the slots 4 and 5 respectively. Further, the holder 1 has its outside surface provided with diametrically opposite, circularly curved edges 8 and 8a which, upon rotation of the holder 1 relative to the dish 3, serve as guide edges for correspondingly shaped edges of slots 9 and recesses 9a respectively, provided in the dish 3. Between the edges of the slots 9 and the circular recess 9a of the dish on the one hand and the thickenings 8 and 8a on the other, the holder 1 and the dish 3 are snap-fitted for movement relative to each other about the Y-axis.

To realize the rotatability of the dish 3 relative to the bowl 2 about the X-axis, two diametrically opposite slots 10 and 11 are provided in the bowl 2, and the dish 3 has its outside surface provided with thickenings 12 and 13 fitting in the slots 10 and 11 respectively. Upon rotation of the dish 3 relative to the bowl 2 about the X-axis, the thickenings 12 and 13 move in the slots 10 and 11 respectively. Further, the bowl 2 is provided with diametrically opposite, circular edges 14 which, upon rotation of the dish 3 relative to the bowl 2, serve as guide edges for correspondingly shaped edges of thickenings 15 provided on the outside surface of the dish 3. Between the thickenings 12, 13 on the one hand and the thickenings 15 on the other, the bowl 2 and the dish 3 are snap-fitted for movement relative to each other about the X-axis.

As extra securement against rotations about the Z-axis perpendicular to the X-axis and the Y-axis, additional locking means in the form of thickenings 16 provided on the outside surface of the dish 3 are present between the dish 3 and the bowl 2, which engage recesses 17 when the holder with dish are mounted in the bowl.

The movement of the holder 1 relative to the dish 3 and that of the dish relative to the bowl 2 is bounded. For this purpose, the holder has an outwardly directed, circular edge 18. Further, viewed in a section perpendicular to the Y-axis, as shown in FIG. 8, the dish 3 is segment-shaped with an apex angle smaller than 180°. When the holder 1 rotates about the Y-axis relative to the dish 3, the upper edges of the dish 3 will, in the two extreme positions, strike the edge 18. Upon rotation of the dish 3 relative to the bowl 2, the thickenings 12, 13 will, in the extreme positions, be arrested by the end edge of the slots 10, 11 or, which is of course also possible, the upper edges of the bowl will be arrested by the projecting edge 18 of the holder.

The bowl 2 further comprises mounting bushes 19. By means of screws passed through these bushes, the bowl can be secured in, for instance, a mirror housing frame for a wing mirror of a vehicle. When, in this practical application, a mirror-adjusting plate 33 with mirror 34 (see FIG. 39) is secured on the holder 1, in particular on the edge 18 hereof, this mirror is manually rotatable about the X-axis and the Y-axis. The position of the holder, the dish and the bowl are shown, one inserted into the other, in FIG. 15, while different views are represented in FIGS. 14, 16 and 17. For clarification, FIGS. 19–24 show the situation where only the holder is secured in the dish for rotation about the Y-axis, and FIGS. 25–30 show the situation where only the dish is secured in the bowl for rotation about the X-axis.

The spherical construction of the holder 1, the dish 3 and the bowl 2 is particularly suitable for fitting a drive system in the holder 1. In the above-mentioned practical application for a wing mirror, this means that in the holder, the drive system is mounted for rotating the mirror and hence the holder about the X-axis and the Y-axis relative to the bowl and hence relative to the mirror housing frame. Because the drive system mounted in the holder 1 must be capable of engaging the bowl 2, relatively large openings 20 are provided in the dish 3. As indicated in FIGS. 31–33, the drive system is mounted in a spherical support 21 that can be screwed down in the holder 1. For that purpose, the holder 1 has screw bushes 22, while the support is at corresponding positions provided with screw holes 23. The holder 1 and the support 21 may also be manufactured as one whole. For the rotation about each of the two axes (the X-axis and the Y-axis), the drive system comprises, in a manner conventional for mirror actuators, a motor in a housing 24 and a transmission mechanism 25. These components form in fact the actuator; in FIG. 39, this actuator, including the housing 24, is designated by 35. Although in the transmission mechanism, a rod-shaped transmission can be incorporated, the transmission in the present embodiment is completely designed as a gear transmission mechanism. By means of this transmission mechanism 25, an adjusting element is displaced in a first direction, while this adjusting element is freely movable in a second direction perpendicular thereto. To enable, in this manner, a rotation of the holder 1 relative to the bowl 2, two slots 26 and 27 are provided in the holder 1, which slots, viewed in the X-Y plane, are perpendicular to each other, while in the bowl 2, two slots 28 and 29 are provided, which slots, viewed in the X-Y plane, are perpendicular to each other, the slot 26 intersecting the slot 28 centrally and perpendicularly, and the slot 27 intersecting the slot 29 centrally and perpendicularly. The slots 28 and 29 in the bowl 2 extend from the circumferential edge to the center of the bowl. To each pair of slots 26, 28 and 27, 29, it applies that an adjusting element 30 is freely movable in the slot 28 and 29 respectively, and motor-drivable in the slot 26 and 27 respectively. However, the reverse is of course also possible, i.e. an adjusting element may also be freely movable in the slot 26 and/or 27 and motor-drivable in the slot 28 and 29 respectively. Although the adjusting elements 30 are provided between the bowl 2 and the holder 3, at the location of the openings 20 in the dish 3, the adjusting elements project through the holder 1 for motor engagement from the inner space of the holder 1. One of the two adjusting elements 30 is shown in more detail in FIG. 38. The free movability of the adjusting elements 30 is realized in that they have their bowl-facing sides provided with a projection 31 engaging the slots 28 and 29. On their side projecting through the holder, the adjusting elements 30 are provided with teeth 32. In the Figure, the adjusting elements are designed as ring segments having inside teeth; a construction as ring segment having, for instance, crown teeth or bevel gear teeth is of course also possible. These teeth then cooperate with a correspondingly formed gear of the gear transmission mechanism.

The direction in which the adjusting elements 30 are motor-drivable may correspond to the two axis directions. However, if stepping motors are used instead of standard dc-motors, it is preferred that the adjusting elements be displaced by motor at an angle of 45° relative the two axis directions; this situation is shown in the embodiment depicted here (see FIGS. 1 and 10). Accordingly, upon rotation about one of the axes, both motors are actuated. Due to the motor displacement of one or both of the adjusting elements and the free movability in directions perpendicular hereto, a rotation of the holder 1 with support relative to the bowl 2 is effected and, accordingly, when used in a wing mirror of a vehicle, a rotation of the mirror-adjusting plate with mirror relative to the mirror housing in which the mirror housing frame with bowl are fixedly mounted.

During assembly, the bowl can already be fixedly secured on the mirror housing frame. The mirror actuator 35 with accessories can be assembled as a separate unit; this unit hence comprises the holder 1, the support 21 containing the motors and the transmission mechanism and the mirror-adjusting plate 33 with mirror 34. Subsequently, such unit can as a whole be snapped in the bowl in a simple manner, with the interposition of the dish.

The movement mechanism according to the invention enables a mirror actuator housing construction wherein the mirror rotation point S (see FIG. 39) is a virtual rotation point, formed by the intersection of the X-axis and the Y-axis, relative to which the actuator housing, i.e. the holder 1 with the support 21 and accessories, is movably connected to the mirror housing frame, including bowl 2, while the mirror-adjusting plate 33 with mirror 34 is fixedly mounted on the actuator housing. Further, in accordance with the invention, a mirror actuator housing construction is enabled wherein the drive means, i.e. the actuator 35, in the actuator housing on the one hand and the mirror-adjusting plate 33 with mirror 34 on the other, are located on either side of the mirror rotation point S of the mirror-adjusting plate 33.

The electrically adjustable mirror construction hitherto described is further particularly suitable for fitting an electric wiring for realizing, apart from the electric mirror adjustment, other functions for the use of the mirror in the mirror housing. Such functions may for instance relate to a mirror heating, electrically dimming of incident light, keeping the mirror water-free through vibrations, and the like. To that end, the housing of the actuator 35 (FIG. 39) comprises an electric plug terminal 36 for a cable 37 realizing the connection to the electric board network of the vehicle. Further, on the mirror-adjusting plate 33, a separate electric terminal 38 is present for an electric connection 39 to the plug terminal 36 on the actuator housing 35, the line 39 forming a fixed looped through-connection of a number of cores of the line 37. Since the actuator housing 35 moves along with the mirror-adjusting plate 33, a vulnerable, flexible construction of the line 39 is no longer necessary.

The invention is not limited to the embodiments described hereinabove with reference to the Figures, but comprises all kinds of modifications hereof, of course in so far as these fall within the protective scope of the following claims. In particular, reference be made to a construction as shown in FIGS. 34–37, where the dish 3 is on either side provided with outwardly bent lips or resilient elements 40, i.e. lips or resilient elements directed both to the bowl 2 and to the holder 1. In this manner, a defined friction between the bowl and the dish and between the dish and the holder can be realized.

What is claimed is:

1. A drive system for a movement mechanism comprising a substantially spherical holder and a substantially spherical bowl which, one inserted into the other, are rotatable elative to each other about a first axis, the X-axis, and a second axis, the Y-axis, which axes lie in a plane substantially coinciding with the plane of the outer edge of the holder or extending parallel thereto, characterized in that the holder, viewed in the X-Y plane, comprises two mutually perpendicular slots provided through the holder, each of said slots having an adjusting element provided therein for motor displacement, said adjusting element further being freely movable in the bowl in a direction, viewed in the X-Y plane, perpendicular to the direction of the relevant slot in the holder, wherein, further, the adjusting element is in an operative connection, through the relevant slot in the holder, with a drive mechanism placed in the holder, said drive mechanism being connected to a motor that is likewise placed in the holder.

2. A drive system according to claim 1, characterized in that the adjusting element is provided with a projection which is freely movable in a slot in the bowl and which extends in a direction, viewed in the X-Y plane, perpendicular to the direction of the relevant slot in the holder.

3. A drive system according to claim 1 or 2, characterized in that the direction of movement of the adjusting elements in the bowl extends from the circumferential edge of the bowl to the center of the bowl.

4. A drive system according to claim 1 or 2, characterized in that the direction of movement of the adjusting elements in the holder extends from the circumferential edge of the holder to the center of the holder.

5. A drive system according to claim 1, characterized in that the adjusting elements are displaceable at an angle of 45° relative to the X-axis and the Y-axis.

6. A drive system according to claim 1, characterized in that the adjusting elements are displaceable at an angle of 90° relative to the X-axis and the Y-axis.

7. A drive system according to claim 1, characterized in that the adjusting elements are displaced by a rod-shaped drive mechanism.

8. A drive system according to claim 1, characterized in that the adjusting elements are toothed elements.

9. A drive system according to claim 8, characterized in that each of the toothed elements is formed by a ring segment having internal teeth.

10. A drive system according to claim 8, characterized in that each of the toothed elements is formed by a ring segment having crown teeth.

11. A drive system according to claim 8, characterized in that each of the toothed elements is formed by a ring segment having bevel gear teeth.

12. A drive system according to claim 1, characterized in that the movement mechanism further comprises a dish located between the holder and the bowl, said dish being connected to the bowl for rotation about the X-axis only and to the holder for rotation about the Y-axis only.

13. A drive mechanism according to claim 1, characterized in that on the holder, an adjusting plate for, for instance, a mirror is fixed, and that the holder with the components arranged therein and fixed thereon can be snapped in the bowl as a unit.

14. A drive mechanism according to claim 13, characterized in that the holder comprises an electric plug terminal, while on the adjusting plate, a separate electrical terminal is present for an electric connection to the plug terminal on the holder.

* * * * *

UNITED STATES PATENT AND TRADEMARK OFFICE
CERTIFICATE OF CORRECTION

PATENT NO. : 6,715,377 B1
DATED : April 6, 2004
INVENTOR(S) : Stefan Frits Brouwer It is certified that error appears in the above-identified patent and that said Letters Patent is hereby corrected as shown below:

Column 5,
Line 41, "elative" should read -- relative --

Signed and Sealed this

Twenty-eighth Day of September, 2004

JON W. DUDAS
*Director of the United States Patent and Trademark Office*